(12) United States Patent
Gorochow

(10) Patent No.: US 12,396,870 B2
(45) Date of Patent: *Aug. 26, 2025

(54) STENT WITH SHAPED WIRES

(71) Applicant: DePuy Synthes Products, Inc., Raynham, MA (US)

(72) Inventor: Lacey Gorochow, Miami, FL (US)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/111,164

(22) Filed: Feb. 17, 2023

(65) Prior Publication Data
US 2023/0190498 A1 Jun. 22, 2023

Related U.S. Application Data

(62) Division of application No. 16/577,567, filed on Sep. 20, 2019, now Pat. No. 11,590,007.

(Continued)

(51) Int. Cl.
*A61F 2/86* (2013.01)
*A61F 2/82* (2013.01)
(Continued)

(52) U.S. Cl.
CPC .............. *A61F 2/86* (2013.01); *A61F 2/82* (2013.01); *A61F 2/90* (2013.01); *A61F 2/91* (2013.01); *A61F 2/885* (2013.01); *A61F 2210/0014* (2013.01); *A61F 2230/0013* (2013.01); *A61F 2240/001* (2013.01);
(Continued)

(58) Field of Classification Search
None
See application file for complete search history.

(56) References Cited

U.S. PATENT DOCUMENTS

| 4,800,882 A | 1/1989 | Gianturco |
| 4,969,458 A | 11/1990 | Wiktor |

(Continued)

FOREIGN PATENT DOCUMENTS

| EP | 0 282 175 A1 | 6/1988 |
| JP | H09-313617 A | 12/1997 |

(Continued)

OTHER PUBLICATIONS

Text of First Office Action and Search Report issued in Chinese Patent Application No. 201910891829.8, Search Report dated Jul. 24, 2023.

(Continued)

*Primary Examiner* — Rebecca S Preston
(74) *Attorney, Agent, or Firm* — TROUTMAN PEPPER LOCKE LLP

(57) ABSTRACT

Stents generally can include a tubular structure having circumferentially positioned undulating wires that extend over a majority of a length of the stent such that the undulations oscillate circumferentially to define a circumference of the stent. The undulations can wrap over and under adjacent undulations to form an interwoven structure. Additionally, or alternatively, adjacent wires can be joined. Wires forming the stent can be cut from elastic tubing such that each wire has a three-dimensional shape.

11 Claims, 10 Drawing Sheets

Related U.S. Application Data

(60) Provisional application No. 62/734,128, filed on Sep. 20, 2018.

(51) Int. Cl.

| | | |
|---|---|---|
| *A61F 2/90* | | (2013.01) |
| *A61F 2/91* | | (2013.01) |
| *A61F 2/88* | | (2006.01) |
| *D03D 1/00* | | (2006.01) |
| *D03D 9/00* | | (2006.01) |

(52) U.S. Cl.
CPC ........ *A61F 2250/0036* (2013.01); *D03D 1/00* (2013.01); *D03D 9/00* (2013.01); *D10B 2509/06* (2013.01)

(56) References Cited

U.S. PATENT DOCUMENTS

| | | | |
|---|---|---|---|
| 5,370,683 | A | 12/1994 | Fontaine |
| 5,707,387 | A | 1/1998 | Wijay |
| 5,925,061 | A | 7/1999 | Ogi et al. |
| 6,027,526 | A | 2/2000 | Limon et al. |
| 6,391,037 | B1 | 5/2002 | Greenhalgh |
| 6,517,570 | B1 | 2/2003 | Lau et al. |
| 6,551,351 | B2 | 4/2003 | Smith et al. |
| 8,277,500 | B2 | 10/2012 | Schmid et al. |
| 8,454,535 | B2 | 6/2013 | Majercak et al. |
| 8,585,643 | B2 | 11/2013 | Vo et al. |
| 8,623,070 | B2 | 1/2014 | Bales et al. |
| 8,721,676 | B1 | 5/2014 | Janardhan et al. |
| 9,039,755 | B2 | 5/2015 | Richter |
| 9,066,827 | B2 | 6/2015 | Schmid et al. |
| 9,232,992 | B2 | 1/2016 | Heidner |
| 9,314,354 | B2 | 4/2016 | Morris et al. |
| 9,408,732 | B2 | 8/2016 | Weier et al. |
| 9,452,068 | B2 | 9/2016 | Schmid et al. |
| 9,486,339 | B2 | 11/2016 | Bales, Jr. et al. |
| 9,532,792 | B2 | 1/2017 | Galdonik et al. |
| 9,532,873 | B2 | 1/2017 | Kelley |
| 9,533,344 | B2 | 1/2017 | Monetti et al. |
| 9,539,011 | B2 | 1/2017 | Chen et al. |
| 9,539,022 | B2 | 1/2017 | Bowman |
| 9,539,122 | B2 | 1/2017 | Burke et al. |
| 9,539,382 | B2 | 1/2017 | Nelson |
| 9,549,830 | B2 | 1/2017 | Bruszewski et al. |
| 9,554,805 | B2 | 1/2017 | Tompkins et al. |
| 9,561,125 | B2 | 2/2017 | Bowman et al. |
| 9,572,982 | B2 | 2/2017 | Burnes et al. |
| 9,579,484 | B2 | 2/2017 | Barnell |
| 9,585,642 | B2 | 3/2017 | Dinsmoor et al. |
| 9,615,832 | B2 | 4/2017 | Bose et al. |
| 9,615,951 | B2 | 4/2017 | Bennett et al. |
| 9,622,753 | B2 | 4/2017 | Cox |
| 9,622,888 | B2 | 4/2017 | Armstrong et al. |
| 9,636,115 | B2 | 5/2017 | Henry et al. |
| 9,636,439 | B2 | 5/2017 | Chu et al. |
| 9,642,675 | B2 | 5/2017 | Werneth et al. |
| 9,655,633 | B2 | 5/2017 | Leynov et al. |
| 9,655,645 | B2 | 5/2017 | Staunton |
| 9,655,989 | B2 | 5/2017 | Cruise et al. |
| 9,662,129 | B2 | 5/2017 | Galdonik et al. |
| 9,662,238 | B2 | 5/2017 | Dwork et al. |
| 9,662,425 | B2 | 5/2017 | Lilja et al. |
| 9,668,898 | B2 | 6/2017 | Wong |
| 9,675,477 | B2 | 6/2017 | Thompson |
| 9,675,782 | B2 | 6/2017 | Connolly |
| 9,676,022 | B2 | 6/2017 | Ensign et al. |
| 9,692,557 | B2 | 6/2017 | Murphy |
| 9,693,852 | B2 | 7/2017 | Lam et al. |
| 9,700,262 | B2 | 7/2017 | Janik et al. |
| 9,700,399 | B2 | 7/2017 | Acosta-Acevedo |
| 9,717,421 | B2 | 8/2017 | Griswold et al. |
| 9,717,500 | B2 | 8/2017 | Tieu et al. |
| 9,717,502 | B2 | 8/2017 | Teoh et al. |
| 9,724,103 | B2 | 8/2017 | Cruise et al. |
| 9,724,526 | B2 | 8/2017 | Strother et al. |
| 9,750,565 | B2 | 9/2017 | Bloom et al. |
| 9,757,260 | B2 | 9/2017 | Greenan |
| 9,764,111 | B2 | 9/2017 | Gulachenski |
| 9,770,251 | B2 | 9/2017 | Bowman et al. |
| 9,770,577 | B2 | 9/2017 | Li et al. |
| 9,775,621 | B2 | 10/2017 | Tompkins et al. |
| 9,775,706 | B2 | 10/2017 | Peterson et al. |
| 9,775,732 | B2 | 10/2017 | Khenansho |
| 9,788,800 | B2 | 10/2017 | Mayoras, Jr. |
| 9,795,391 | B2 | 10/2017 | Saatchi et al. |
| 9,795,496 | B2 | 10/2017 | Armstrong et al. |
| 9,801,980 | B2 | 10/2017 | Karino et al. |
| 9,808,599 | B2 | 11/2017 | Bowman et al. |
| 9,833,252 | B2 | 12/2017 | Sepetka et al. |
| 9,833,604 | B2 | 12/2017 | Lam et al. |
| 9,833,625 | B2 | 12/2017 | Waldhauser et al. |
| 11,590,007 | B2* | 2/2023 | Gorochow ............... A61F 2/91 |
| 2001/0003801 | A1 | 6/2001 | Strecker |
| 2002/0022875 | A1* | 2/2002 | Strecker ................ A61F 2/90 623/1.15 |
| 2002/0173839 | A1 | 11/2002 | Leopold et al. |
| 2003/0083735 | A1 | 5/2003 | Denardo et al. |
| 2003/0114920 | A1 | 6/2003 | Caro et al. |
| 2003/0171801 | A1 | 9/2003 | Bates |
| 2004/0039435 | A1* | 2/2004 | Hancock .......... A61B 17/12022 623/1.2 |
| 2006/0064151 | A1 | 3/2006 | Guterman |
| 2006/0136041 | A1 | 6/2006 | Schmid et al. |
| 2007/0208409 | A1 | 9/2007 | Quigley |
| 2008/0281350 | A1 | 11/2008 | Sepetka |
| 2010/0324649 | A1 | 12/2010 | Mattsson |
| 2011/0054590 | A1 | 3/2011 | Leopold et al. |
| 2012/0283768 | A1 | 11/2012 | Cox et al. |
| 2013/0226282 | A1 | 8/2013 | Ahn et al. |
| 2014/0135812 | A1 | 5/2014 | Divino et al. |
| 2014/0200607 | A1 | 7/2014 | Sepetka et al. |
| 2014/0330367 | A1* | 11/2014 | Thapliyal .............. A61F 2/2415 623/2.11 |
| 2017/0007264 | A1 | 1/2017 | Cruise et al. |
| 2017/0007265 | A1 | 1/2017 | Guo et al. |
| 2017/0020670 | A1 | 1/2017 | Murray et al. |
| 2017/0020700 | A1 | 1/2017 | Bienvenu et al. |
| 2017/0027640 | A1 | 2/2017 | Kunis et al. |
| 2017/0027692 | A1 | 2/2017 | Bonhoeffer et al. |
| 2017/0027725 | A1 | 2/2017 | Argentine |
| 2017/0035436 | A1 | 2/2017 | Morita |
| 2017/0035567 | A1 | 2/2017 | Duffy |
| 2017/0042548 | A1 | 2/2017 | Lam |
| 2017/0049596 | A1 | 2/2017 | Schabert |
| 2017/0071737 | A1 | 3/2017 | Kelley |
| 2017/0072452 | A1 | 3/2017 | Monetti et al. |
| 2017/0079671 | A1 | 3/2017 | Morero et al. |
| 2017/0079680 | A1 | 3/2017 | Bowman |
| 2017/0079766 | A1 | 3/2017 | Wang et al. |
| 2017/0079767 | A1 | 3/2017 | Leon-Yip |
| 2017/0079812 | A1 | 3/2017 | Lam et al. |
| 2017/0079817 | A1 | 3/2017 | Sepetka et al. |
| 2017/0079819 | A1 | 3/2017 | Pung et al. |
| 2017/0079820 | A1 | 3/2017 | Lam et al. |
| 2017/0086851 | A1 | 3/2017 | Wallace et al. |
| 2017/0086996 | A1 | 3/2017 | Peterson et al. |
| 2017/0095259 | A1 | 4/2017 | Tompkins et al. |
| 2017/0100126 | A1 | 4/2017 | Bowman et al. |
| 2017/0100141 | A1 | 4/2017 | Morero et al. |
| 2017/0100143 | A1 | 4/2017 | Granfield |
| 2017/0100183 | A1 | 4/2017 | Iaizzo et al. |
| 2017/0113023 | A1 | 4/2017 | Steingisser et al. |
| 2017/0147765 | A1 | 5/2017 | Mehta |
| 2017/0151032 | A1 | 6/2017 | Loisel |
| 2017/0165062 | A1 | 6/2017 | Rothstein |
| 2017/0165065 | A1 | 6/2017 | Rothstein et al. |
| 2017/0165454 | A1 | 6/2017 | Tuohy et al. |
| 2017/0172581 | A1 | 6/2017 | Bose et al. |
| 2017/0172766 | A1 | 6/2017 | Vong et al. |
| 2017/0172772 | A1 | 6/2017 | Khenansho |
| 2017/0189033 | A1 | 7/2017 | Sepetka et al. |
| 2017/0189035 | A1 | 7/2017 | Porter |

(56) References Cited

U.S. PATENT DOCUMENTS

| | | |
|---|---|---|
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304092 A1 | 10/2017 | Hong et al. |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |

FOREIGN PATENT DOCUMENTS

| | | |
|---|---|---|
| JP | 2016-517751 A | 6/2016 |
| JP | 2016-129575 A | 7/2016 |
| WO | 2009/077845 A2 | 6/2009 |

OTHER PUBLICATIONS

Partial European Search Report issued in corresponding European Patent Application No. 19 19 8448 mailed Feb. 5, 2020.
Translation of Japanese Office Action in corresponding JP Appln. No. 2023-193007, dated Aug. 27, 2024, and submitted herewith.
Machine Translation of Japanese Office Action date drafted Aug. 4, 2023, in corresponding JP Appln. No. 2019-170161, and submitted herewith.

* cited by examiner

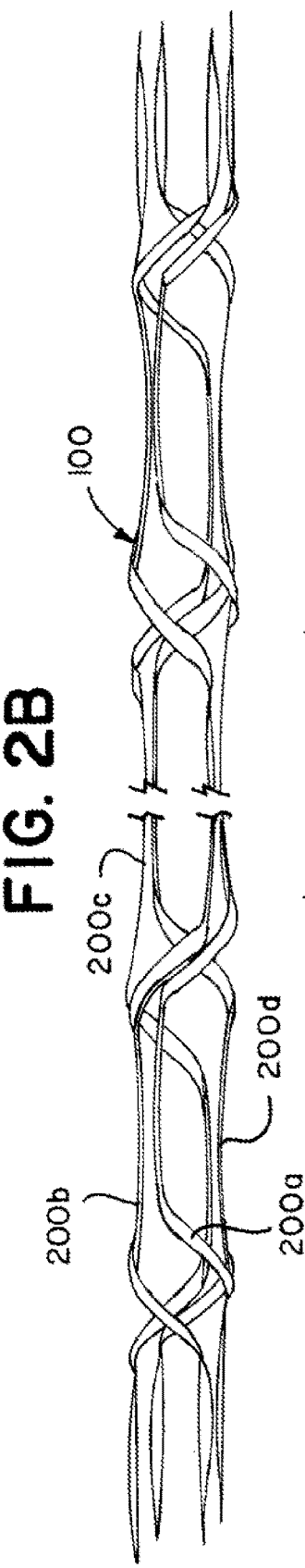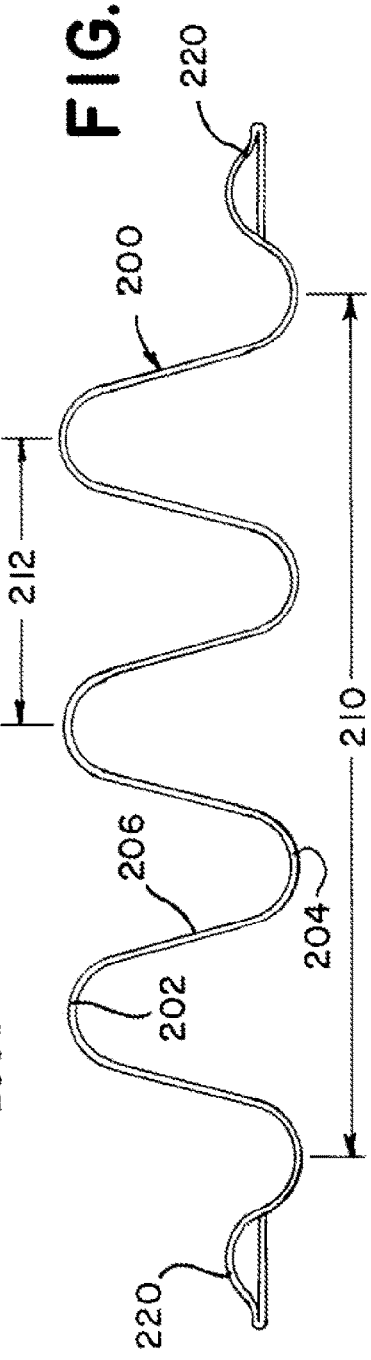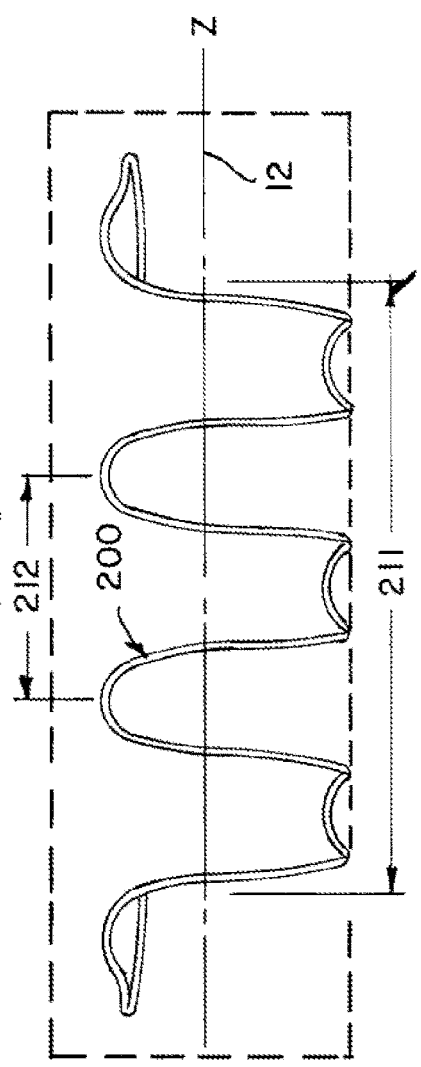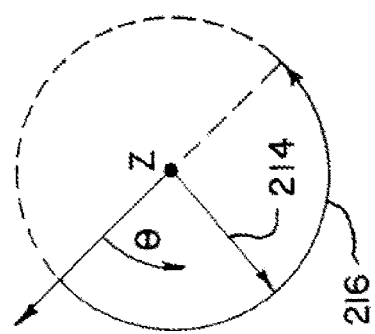

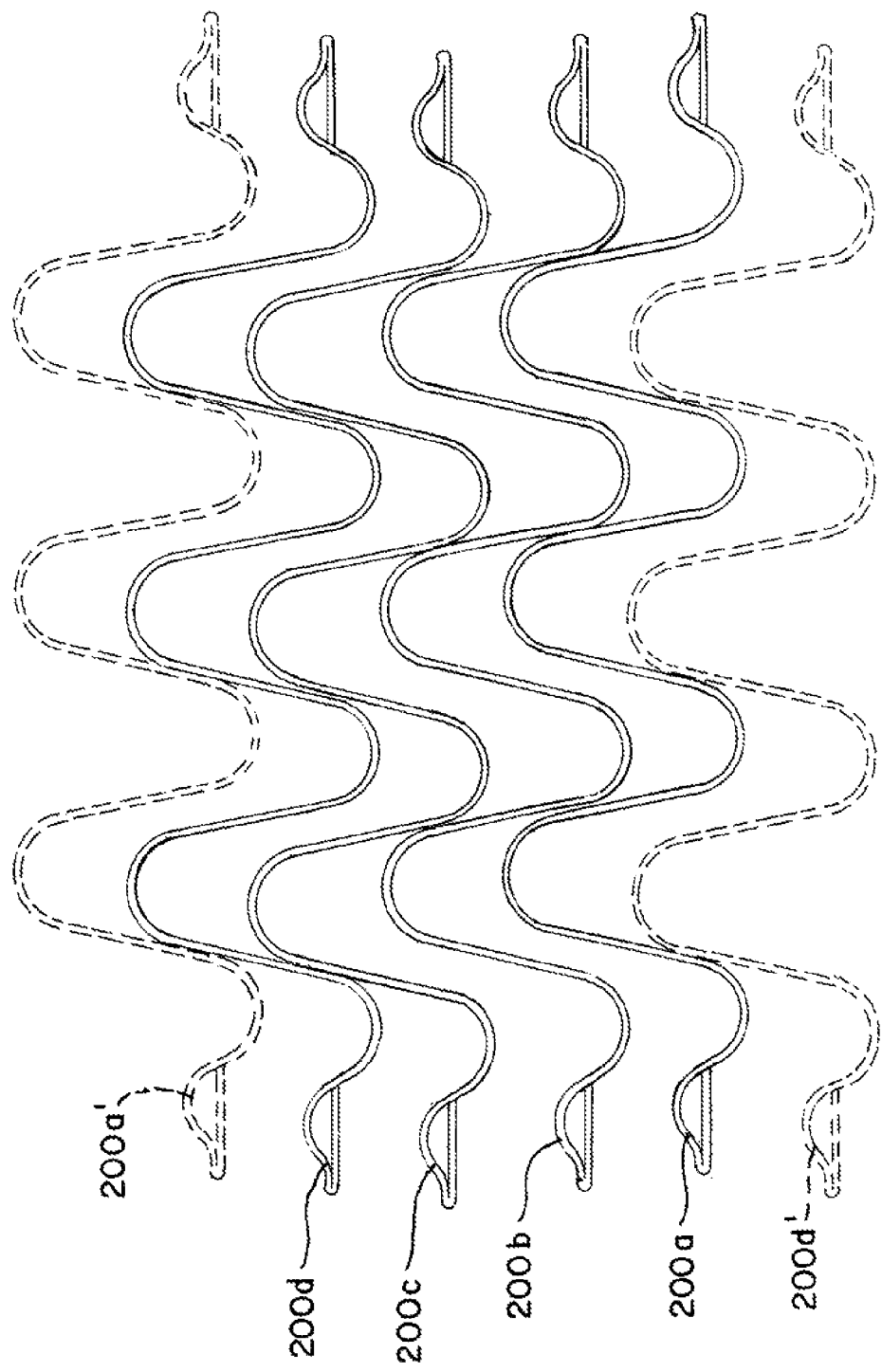

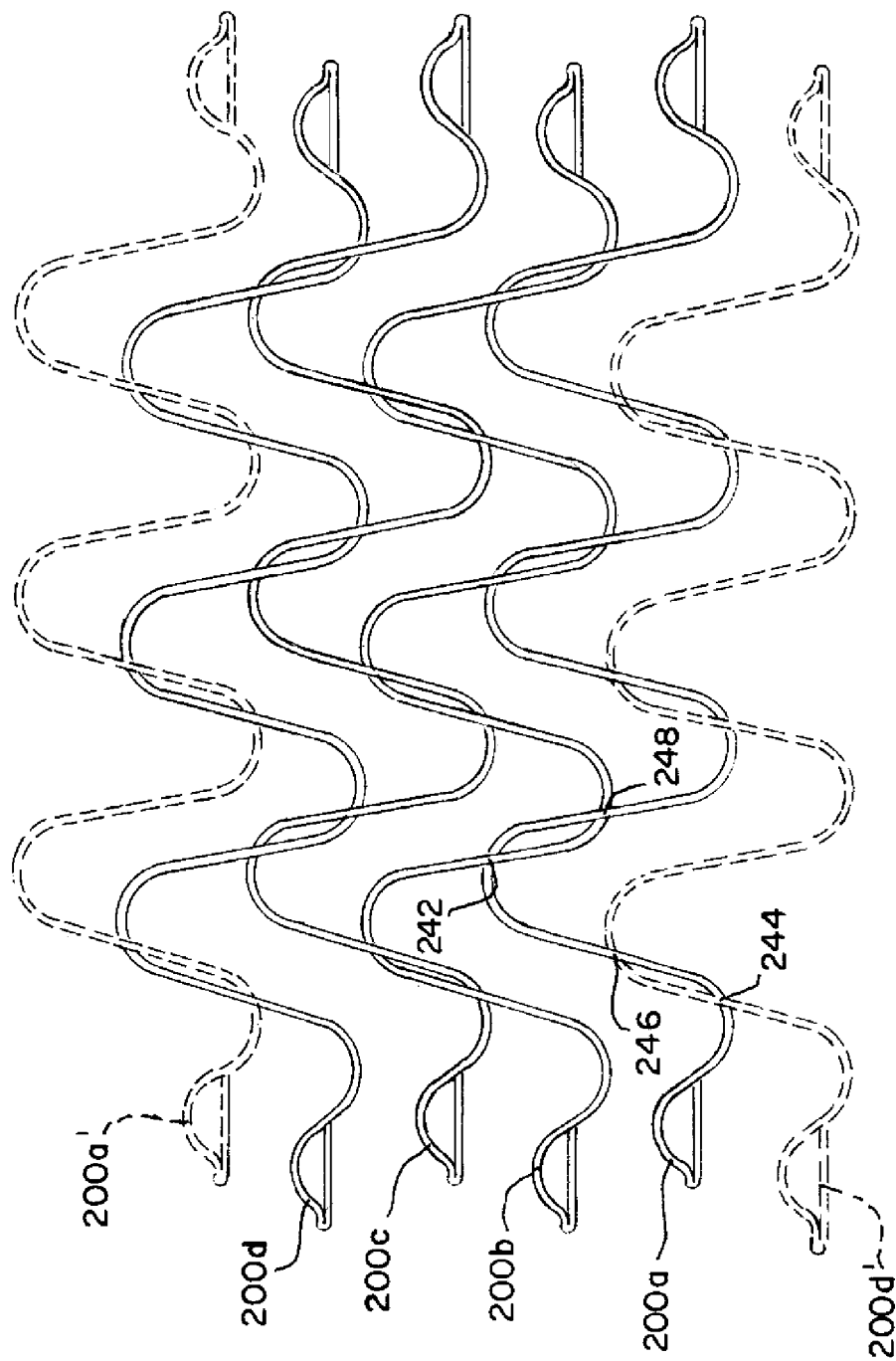

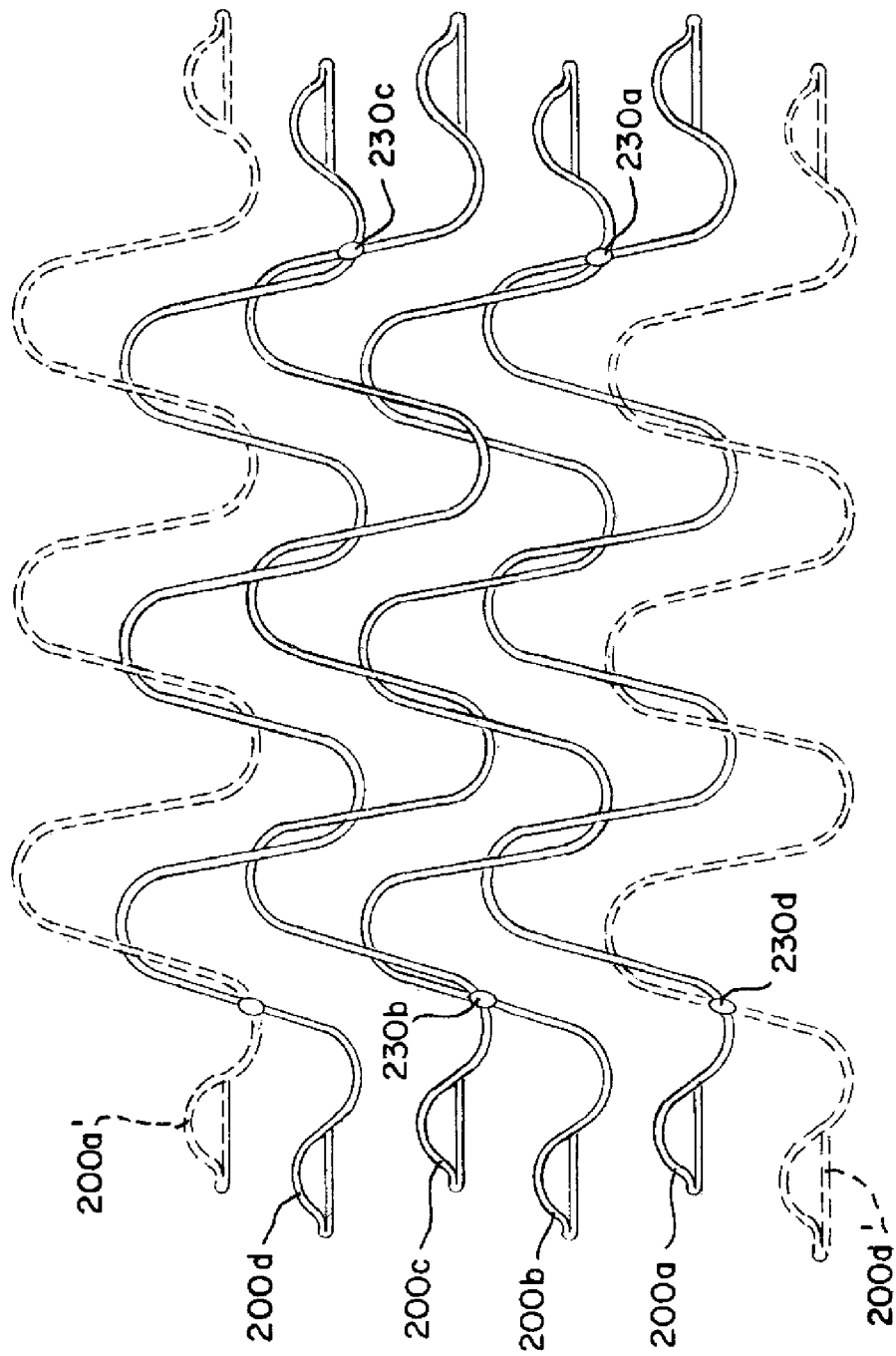

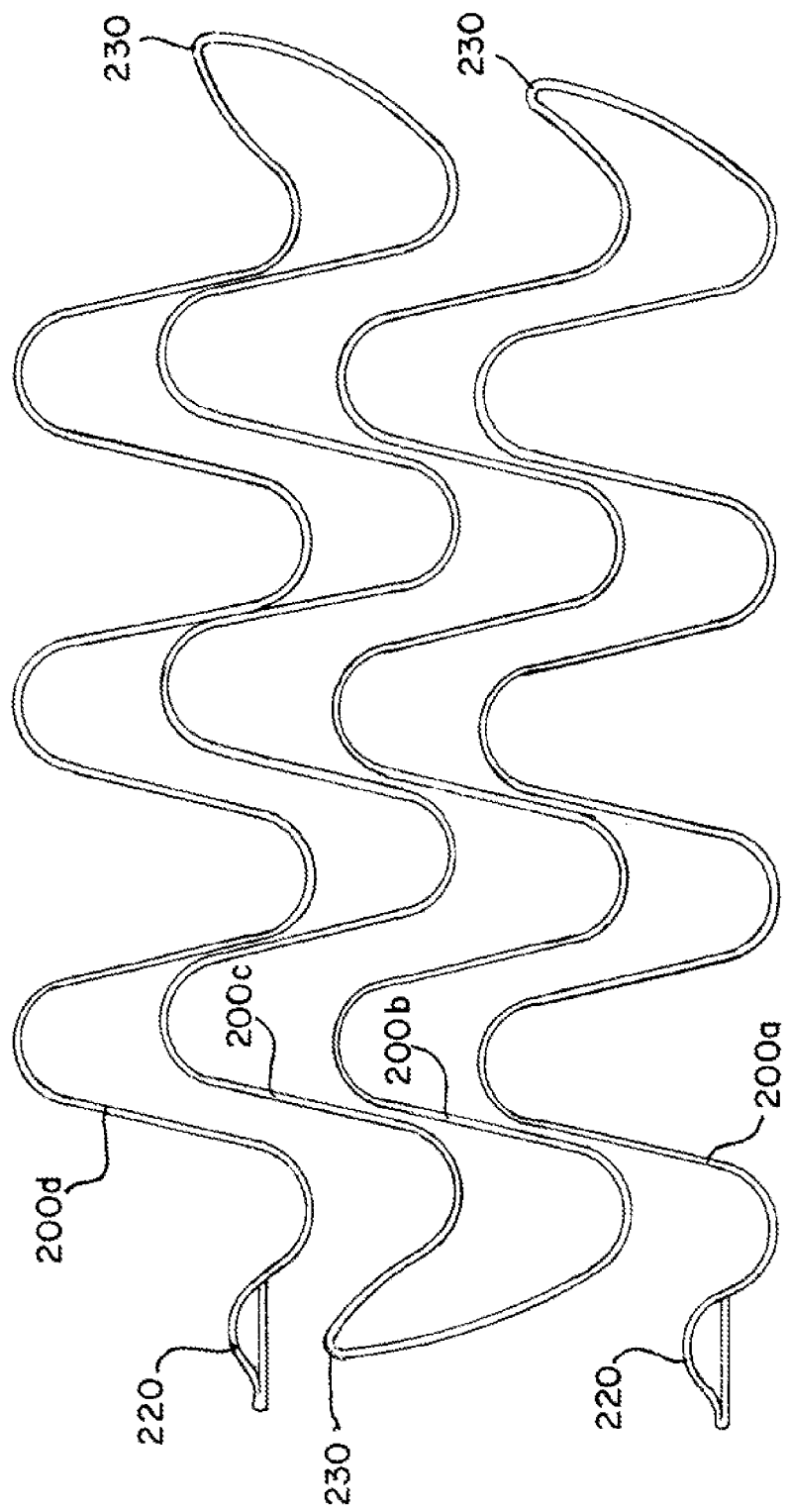

STENT WITH SHAPED WIRES

CROSS REFERENCE TO RELATED APPLICATIONS

This application is a divisional of U.S. patent application Ser. No. 16/577,567 filed Sep. 20, 2019, which claims the benefit of U.S. Provisional Application No. 62/734,128 filed on Sep. 20, 2018, which prior applications are hereby incorporated by reference in their entirety herein into this application as if set forth in full.

FIELD OF INVENTION

The present invention generally relates to implantable stent medical devices, methods for manufacturing the same, and more particularly, to novel stent structures.

BACKGROUND

Medical stents are used for supporting, maintaining, or repairing a lumen, passageway or opening in a living body. Stent design is unique to location and objective of the treatment as the stent must be flexible enough in a collapsed state to navigate body lumen to arrive at a treatment site, structurally robust enough in an implanted state to provide the required structural support to repair the treatment site, and flexibly expandable to have high conformity in treatment sites having tapered, bent, or other non-linear or non-tubular shapes. Flexibility, structural integrity, and conformability are often competing design goals that will vary depending on the location of the treatment site, goal of the treatment, and geometry of the treatment site.

Wire, or braided stents, are typically braided from flexible wires to form a tube of wires that wrap helically around a center axis of the stent, with roughly half of the wires wrapping clockwise, and the other half wrapping counterclockwise such that wires extending in opposite direction wrap over and under each other diagonally in an alternating fashion. Wire stents can be very flexible, can achieve high conformity within a body lumen containing a bend, and can resist kinking; however, the wire stents typically lack structural integrity to apply outward force radially against a lumen wall that is required in some treatments.

A general strategy for stent design when structural integrity is desired involves laser cutting patterns from a length of elastic tubing, typically made of a memory shape metal such as Nitinol or a Nitinol alloy. In general, material is removed from the tubing to form a cell pattern. Generally speaking, enough material must remain so that the overall structural integrity of the laser cut stent is sufficient to apply the required outward force against a lumen wall once implanted. Material is strategically removed to increase the flexibility of the stent for delivery to a treatment site and conformity to lumen walls in treatment sites including a bend or other non-uniform wall structure. In many stent designs, patterns are cut to form rings that are substantially circumferential connected longitudinally by bridge struts. In such designs, bridge struts are added to achieve greater structural integrity and taken away to achieve greater flexibility.

Attempts have been made to design a stent having greater flexibility and kink resistance compared to stents cut from elastic tubing and greater structural integrity compared to wire stents. One such strategy involves cutting elastic tubing to for a single helical structure that wraps circumferentially around the body of the stent such that adjacent windings of the helix are longitudinally interconnected with bridge struts (e.g. U.S. Pat. No. 5,925,061). Another strategy involves cutting a sheet of material to form a lattice strand that can be wrapped as a single helix about a mandrel and adjacent windings are subsequently interconnected (e.g. U.S. Pat. No. 5,370,683). Although such designs typically can achieve greater flexibility compared to a laser cut tubular stent utilizing circumferential rings, it is at the cost of structural integrity; and although such designs can achieve greater structural integrity compared to wire stents, they cannot achieve the conformability and kink resistance of most wire stents.

There therefore exists a need for alternative stent designs for achieving flexibility, structural integrity, and conformability to meet the needs of a variety of treatment goals at a variety of treatment sites having a variety of anatomical geometries.

SUMMARY

Disclosed herein are various exemplary stents of the present invention that can address the above needs. The stents generally can include a tubular structure having circumferentially positioned undulating wires that extend over a majority of a length of the stent such that the undulations oscillate circumferentially, and the undulations of the wires collectively define a circumference of the stent. The undulations can wrap over and under adjacent undulations to form an interwoven structure. Additionally, or alternatively, adjacent wires can be joined.

An example stent can include a stent length measured from a first open end to a second open end, two or more wires each having a three-dimensional oscillating portion that extends over most of the stent length and is movable independent of the oscillating portion of every other of the one or more wires. The oscillating portion for each wire can have an oscillating portion length measured parallel to a z-axis, a curvature extending circumferentially through an arc of less than 360° about the z-axis at a constant radius from the z-axis, and a waveform that oscillates over the length of the oscillating portion through the arc. The oscillating portion of each of the one or more wires can be movable independent of every other of the one or more wires.

Another example stent having a circumference and a length can include two or more wires, each wire having a three-dimensional waveform that oscillates circumferentially within an arc about a z-axis parallel to the stent length, such that each waveform extends parallel to the z-axis through a majority of the stent length, maintaining a substantially constant radial distance from the z-axis. The wires of the stent can be positioned circumferentially adjacent each other about the circumference of the stent to define the circumference of the stent. Each wire can be movable along a majority of the length of the stent independently of every other wire in the stent.

Another example stent having a tubular structure with a circumference and a length can include a plurality of wires positioned around the circumference of the stent. Each wire can be independently formed, can undulate circumferentially to form a wave pattern that extends over a majority of the length of the stent, can pass under an over an adjacent wire in a repeated fashion while maintaining an adjacent position to the adjacent wire over the majority of the length of the stent, and can intertwine circumferentially with other wires to form the tubular stent.

Another example stent having tubular structure can include circumferentially positioned undulating wires that extend over a majority of a length of the stent. The wires can each have undulations that oscillate circumferentially. The undulations of each wire can recess circumferentially within undulations of an adjacent wire such that the circumferential positioning of the undulating wires can define a circumference of the stent, and the circumferential positioning of the undulating wires can solely define the circumference of the stent absent any additional structures to define the circumference of the stent.

In any of the example stents, each wire of the stent can be independently formed from every other wire of the stent. Each wire of the stent can be joined at one or more locations to a circumferentially adjacent wire. The stent can include a first joint affixing a first wire to a second wire near the first open end. The first joint can be the only affixed joint between the first wire and the second wire. Additionally, or alternatively, to affixing adjacent wires, the first wire can cross under and cross over the second wire within one period of oscillation of the waveform of the first wire.

In any of the example stents, the stent can include a first end structure positioned adjacent the first open end, extending between the first open end and the oscillating portion of the stent, and the stent can include a second end structure positioned adjacent the second open end, extending between the second open end and the oscillating portion. One or both of the first and second end structures can have an atraumatic shape.

In any of the example stents, a wire of the stent can have a width that varies along the length of the stent.

In any of the example stents, one or more of the wires can include a memory shape material. At least one wire can have a pre-determined three-dimensional shape curved along an arc, the three-dimensional shape having a wave pattern that undulates within the arc.

An example method for manufacturing a stent including any of the example stents described herein can include the steps of providing an elastic tubing, cutting the tubing to form a plurality of substantially similar wave patterns, separating each of the plurality of wave patterns from the tubing, positioning each wave pattern to extend across a majority of the length of the stent, and forming a majority of a tubular stent body from the plurality of wave patterns. Each wave pattern can have an amplitude extending circumferentially through an arc within a circumference of the tubing from which it is cut, an axis extending along at least a portion of a length of the tubing over which the wave pattern repeats, and a curved inner surface being the cut portion of the luminal surface of the tubing.

Another example method for manufacturing a stent including any of the example stents described herein can include the steps of providing an elastic tubing having a circumference and a length, cutting individual wires from the tubing such that each wire has a wave pattern oscillating peak-to-peak across a portion of the circumference, and weaving the wires to form a tube shape.

Any of the example methods can include any combination of the steps of cutting individual wires from the provided tubing such that each wire has a wave pattern that oscillates peak-to-peak across a portion of the circumference, separating the cut wires from the tubing such that the wires are disconnected from each other, joining a first wire to a second wire at one or more locations, joining a first wire to a second wire near an end of the stent body, and/or intertwining each wire with a clockwise adjacent wire and a counterclockwise adjacent wire.

BRIEF DESCRIPTION OF DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 2B is a side view of the stent of FIG. 2A in a collapsed state according to the present invention;

FIG. 3A is a two-dimensional depiction of a wire of a stent according to the present invention;

FIG. 3B is a three-dimensional depiction of the wire of FIG. 3A according to the present invention;

FIG. 3C is a schematic of a coordinate system for describing the three-dimension shape of a wire of a stent such as the wire depicted in FIG. 3B;

FIGS. 4 to 9 are two-dimensional depictions of wires of a stent illustrating example placements of wires around a circumference of the stent according to the present invention;

DETAILED DESCRIPTION

Various exemplary stents are described herein that can address the above needs. In general, a stent can have a generally tubular structure with circumferentially positioned undulating wires extending over a majority of a length of the stent. Undulations of each wire can oscillate circumferentially, and the undulations of a wire can recess within undulations of adjacent wires, such that the recession of each wire into each other defines a circumference of the stent. Adjacent wires can be joined at few locations, such as at the ends, or not at all, such that individual wires are movable independent from every other wire. Additionally, or alternatively, the undulations can wrap over and under adjacent undulations to form an interwoven structure.

Generally, example stents described herein can be cut from a metal tube and can be prepared by cutting the tube into separate wires that retain a helical curvature from the tube wall from which they are cut. Wires can be cut from the tube to be substantially independent from one another, and these wires can be braided, woven, or otherwise intertwined to form a tubular shape. In some applications it may be desirable to utilize between eight and sixteen laser cut wires to form a stent with desired flexibility, structural integrity, and conformability. Wires in some example stents can move independently of each other to some extent; for example, the wires of an example stent can be movable like how wires in known braided or woven structures are generally movable independent of each other. Additionally, or alternatively, wires in some example stents can be welded or otherwise joined to each other at one or more locations along a length of each of the wires. Joined wires can form an interlocking structure and can increase structural integrity of the stent.

Because wires of some example stents can be made substantially movable to each other, some example stents can have improved flexibility and kink resistance compared to known laser cut tube designs and can achieve flexibility and kink resistance like known wire braid stent designs. Because the wires of some example stents can be cut from a metal tube, the wires of an example stent can provide greater radial force compared to wires of known wire braid stent designs, the wires of the stent can be designed to have an atraumatic end structure (which is typically not achievable by using cut wires in known wire braid stent designs), and the stent can have wires that vary in thickness and shape along the length of the stent (which is generally not possible in known wire braid stent designs that utilize constant diameter wires). A potential application of some example stents can be supporting embolic coils within an aneurysm at a treatment site that requires navigation of torturous anatomy to reach.

Figure 1:
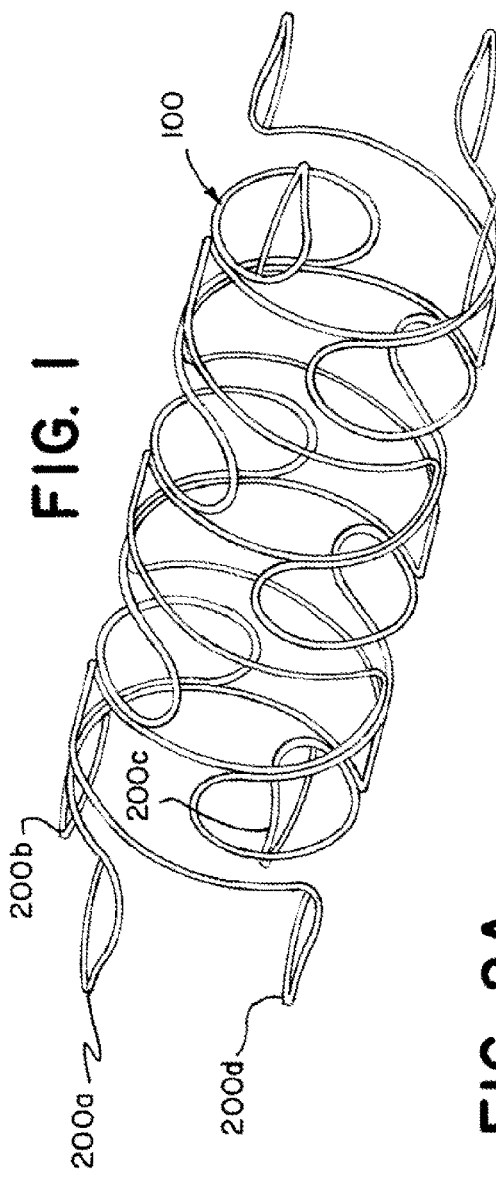
FIG. 1 is a three-dimensional perspective view of a stent according to the present invention.

FIG. 1 is a three-dimensional perspective view of a stent 100 having four wires 200a, 200b, 200c, 200d. As will be appreciated and understood a stent 100 can include as few or as many wires as required to achieve a desired flexibility, structural integrity, and conformability. A stent having a greater number of wires may be required, for example, when treating a body lumen having a larger diameter. A stent can also be designed to have a space between wires through which a microcatheter for delivering an embolic implant can passthrough; in which case, it may be desirable to create pores between wires that are small enough to provide enough structural support but large enough so a coiling microcatheter can fit through a pore. In some applications it may be desirable to utilize between eight and sixteen laser cut wires.

Figure 2A:
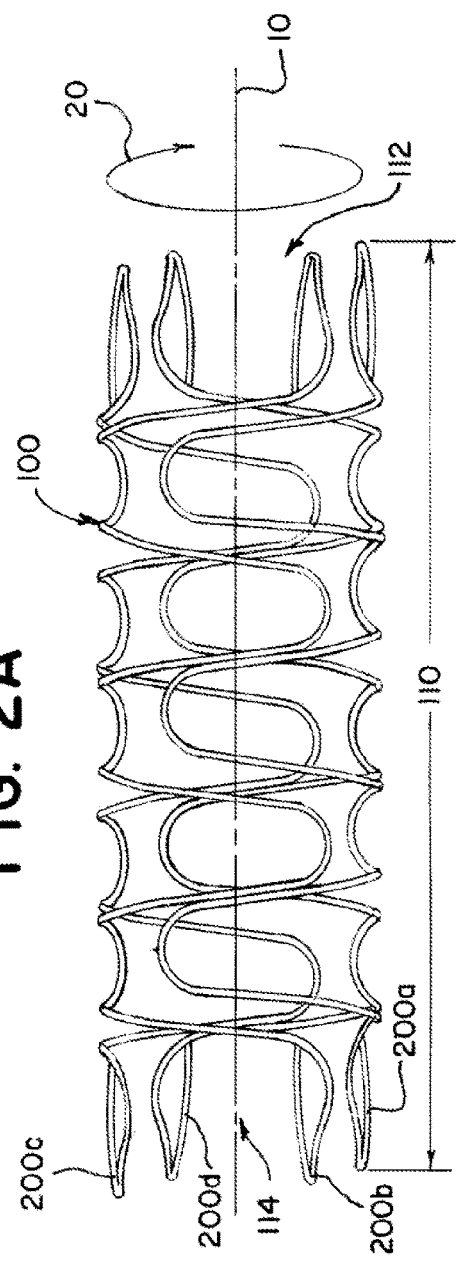
FIG. 2A is a side view of a stent in an expanded state according to the present invention.

FIG. 2A is a side view of a stent 100 in an expanded state like that of FIG. 1 having four wires 200a, 200b, 200c, 200d. The stent 100 can have a substantially tubular body shape with a first open end 112, a second open end 114, and a length 110 extending from the first open end 112 to the second open end 114 in a longitudinal direction 10. The stent 100 can be designed to have a length to meet the needs of the treatment, for example, the length 110 can be sized larger than a neck of an aneurysm such that aneurysms having a larger neck opening could be treated with a longer stent. The tubular body shape of the stent 100 can have a substantially uniform circumference 20 along its length 110 in an expanded state. Alternatively, (not shown) a stent can have a tubular body shape having a large circumference at a first open end that tapers to a smaller circumference at a second open end. Such a tapered design can be advantageous for treating tapered body lumens, for example.

FIG. 2B is a side view of the stent of FIG. 2A in a collapsed state. In the collapsed state, the stent 100 can be sized to be delivered through a microcatheter to a treatment site within a vasculature. Because the stent 100 can be made of a small number of wires, and each wire 200a, 200b, 200c, 200d can be stretched in the longitudinal direction 10 to occupy a small cross-sectional profile, an advantage of the stent 100 is that it can be collapsed to a thinner dimension than a laser cut tubular type stent. Laser cut tubular type stents typically have little ability to stretch lengthwise. The thinner collapsed dimension, in some applications, can allow the stent 100 to be delivered to a treatment site through a smaller catheter, therefore reaching treatment sites that may be challenging or impossible to reach with other stent designs.

A wire 200 is illustrated in FIG. 3A in two dimensions and in FIG. 3B in three dimensions. The wire 200 has a three-dimensional shape as illustrated in FIG. 3B; the two-dimensional illustration of FIG. 3A is provided to aid visualization and discussion of the wire 200. Referring collectively to FIGS. 3A and 3B, a wire 200 can have an oscillating portion 210 having an oscillating portion length 211 measured parallel to a z-axis 12. The oscillating portion 210 can have a waveform that repeats over the length 211 of the oscillating portion 210, repeating with a period of oscillation 212. The waveform can be sinusoidal having a series of peaks 202, troughs 204, and intermediate segments 206 extending between the peaks 202 and troughs 204. The oscillating portion 210 can extend over a majority of a length of the stent, and the wire 200 can also have end structures 220 at the ends of each wire 200. Each end structure 220 can have an atraumatic shape.

FIG. 3C is a schematic of a cylindrical coordinate system for describing the three-dimension shape of a wire 200 of a stent 100 such as the wire depicted in FIG. 3B. In the cylindrical coordinate system, the z-axis 12 is understood to be perpendicular to the page, positioned at the center of the circle illustrated in FIG. 3C. In general, a position of a point in the cylindrical coordinate system can be defined by the coordinates r, θ, and z, where the r coordinate defines a distance from the z-axis, the θ coordinate defines an angle from the r-axis, and the z coordinate defines a linear position along the z-axis. A tube would therefore include points where r is equal to a constant, R over given length in the z-axis, and an arc in said tube would be confined to an angle, or range of values for θ, the angle being less than 360°. The example wire 200 illustrated in FIG. 3B can therefore be described as having a curvature extending circumferentially through an arc 216 of approximately 180° that maintains a substantially constant radius 214 from the z-axis. The waveform can be described as oscillating circumferentially, confined within the arc of the curvature, extending in the z-direction over the length 211 of the oscillating portion 210. Referring to FIG. 3A, an amplitude of the waveform can be described as the distance between the peaks 202 and the troughs 204. Referring to FIGS. 3B and 3C, the amplitude of the waveform can therefore be expressed as a function of the arc of the curvature 216 and the radius 214. As will be appreciated and understood, the curvature could be wider or narrower to achieve desired properties of the stent. For example, a waveform having a larger amplitude can result in an overall stent design having greater flexibility while a waveform having a smaller amplitude can result in an overall stent design that is easier to deliver through a microcatheter.

Referring to FIGS. 3B and 3C, the wire can be formed by cutting the wire from a portion of elastic tubing. The tubing can have a radius 214, and the tubing can be cut so that the resulting wire 200 has an oscillating portion that maintains the radius 214 of the tubing. The wire 200 can be cut from an arc defined by at least a portion of the circumference of the tubing so that the resulting wire 200 oscillates within the arc 216, and the resulting wire can have a wave pattern that oscillates peak-to-peak across the cut portion of the circumference of the tube.

The tubing can have a lumen with an inner luminal surface. The wire 200 can be cut from the tubing to have an inner surface that is cut from the luminal surface of the tubing. The wire 200 can be cut from the tubing such that a majority of the oscillating portion 210 is movable independent of oscillating portions 210 of other wires. The wire 200, once cut, can be separated from the tubing to form an independently formed wire 200.

FIGS. 4 to 9 are two-dimensional depictions of wires of a stent illustrating example placements of wires around a circumference of the stent. The illustrations are provided in two dimensions for discussion and visualization. Referring collectively to FIGS. 4 to 8, the illustrations depict the placement of four wires 200a, 200b, 200c, 200d circumferentially to form a stent. The bottom wire 200a is redrawn as a dashed wire 200a' above the top wire 200d, and the top wire 200d is redrawn as a dashed wire 200d' below the bottom wire 200a to illustrate the placement and connection of the wires shown as the top and bottom wires 200d, 200a in a three-dimensional stent.

The wires 200a, 200b, 200c, 200d can be cut from tubing, and each wire can be positioned to define a circumference of a stent. Wires can be positioned such that each oscillating portion 210 extends across a length of the stent. Inner curved surface of each oscillating portion 210 of each wire 200a, 200b, 200c, 200d can be aligned to collectively form the circumference of the stent. Wires 200a, 200b, 200c, 200d can be joined and/or woven to form a tube shape.

FIG. 4 is a two-dimensional illustration of four wires placed to define a circumference of a stent like the stents depicted in FIGS. 1 and 2A. Each wire can be recessed circumferentially within undulations of circumferentially adjacent wires such that the circumferential positioning of the undulating wires defines a circumference of the stent. Each wire can be independently formed and at least to some extent, movable compared to every other wire.

Figure 5:
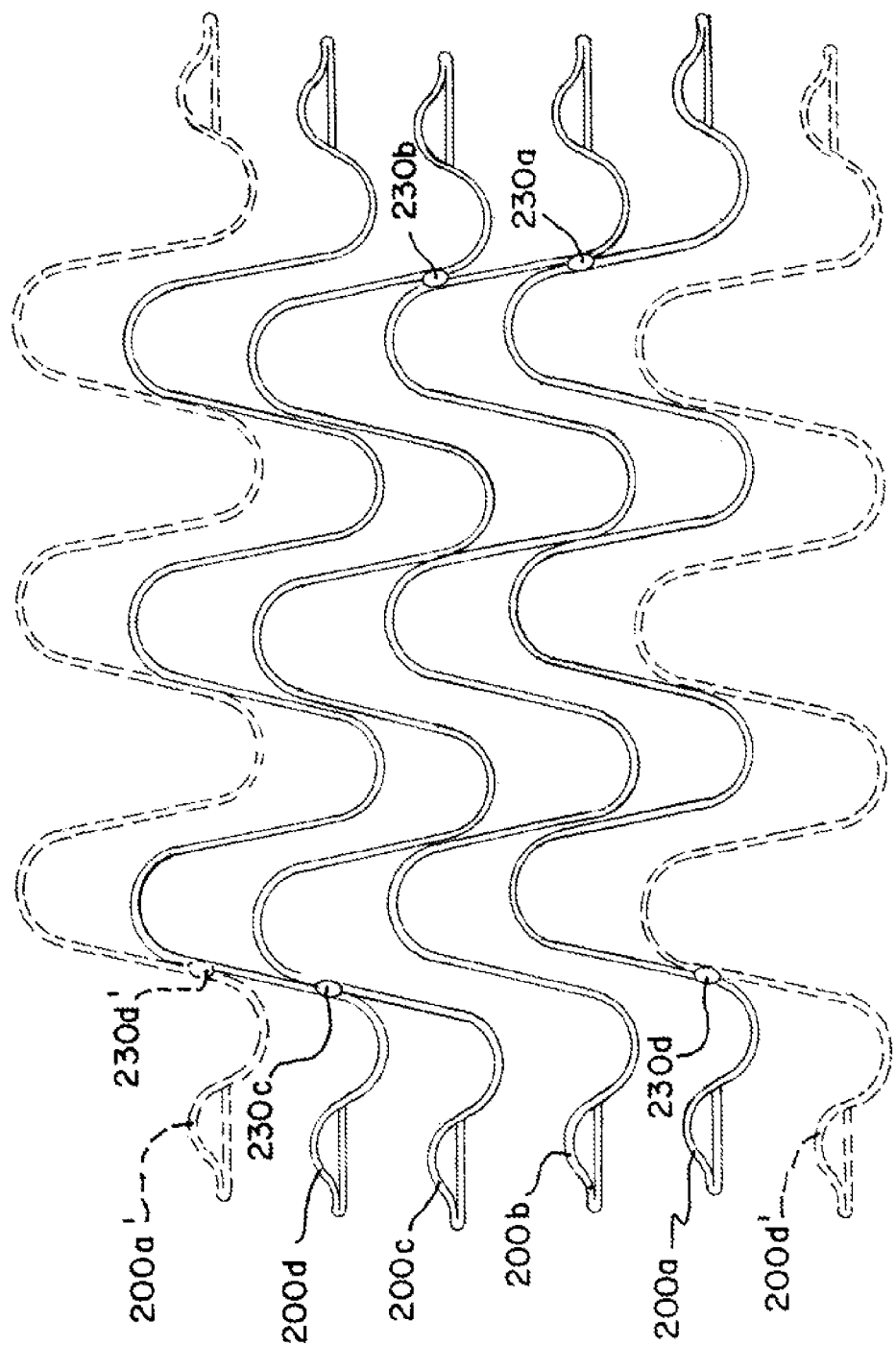

FIG. 5 is a two-dimensional illustration of four wires placed to define a circumference of a stent like the pattern shown in FIG. 4. Each wire can be connected to each adjacent wire by a single joint 230a, 230b, 230c, 230d, 230d'. As shown, a first joint 230c can join a first wire 200c to a second wire 200d adjacent to the first wire 200c, and the first joint 230c can be the only affixed joint between the first wire 200c and the second wire 200d. The first wire 200c can also be joined to a third wire 200b with a second joint 230b. As shown, each wire 200a, 200b, 200c, 200d can be joined to its two adjacent neighbors by a single joint for each neighbor. Minimal connections 230a, 230b, 230c, 230d can allow the wires to move independently of each other over a majority of the length of the stent.

As will be appreciated and understood, each joint can be formed by any conventional means such as welding, brazing, soldering, gluing, tying, etc. Alternatively, or additionally, a stent can be cut from a single piece of tubing such that the joints 230a, 230b, 230c, 230d are uncut portions of the tubing. In one example, a wire 200a, 200b, 200c, 200d joined to a neighboring wire by an uncut tubing portion would not be completely separated from the neighbor during manufacturing. However, the uncut portion can be placed at a joint location 230a, 230b, 230c, 230d like those shown in FIGS. 5 and 6 and described herein to allow the wire 200a, 200b, 200c, 200d to be movable independently of the neighbor wire and other wires over a majority of the length of the stent.

Figure 6:
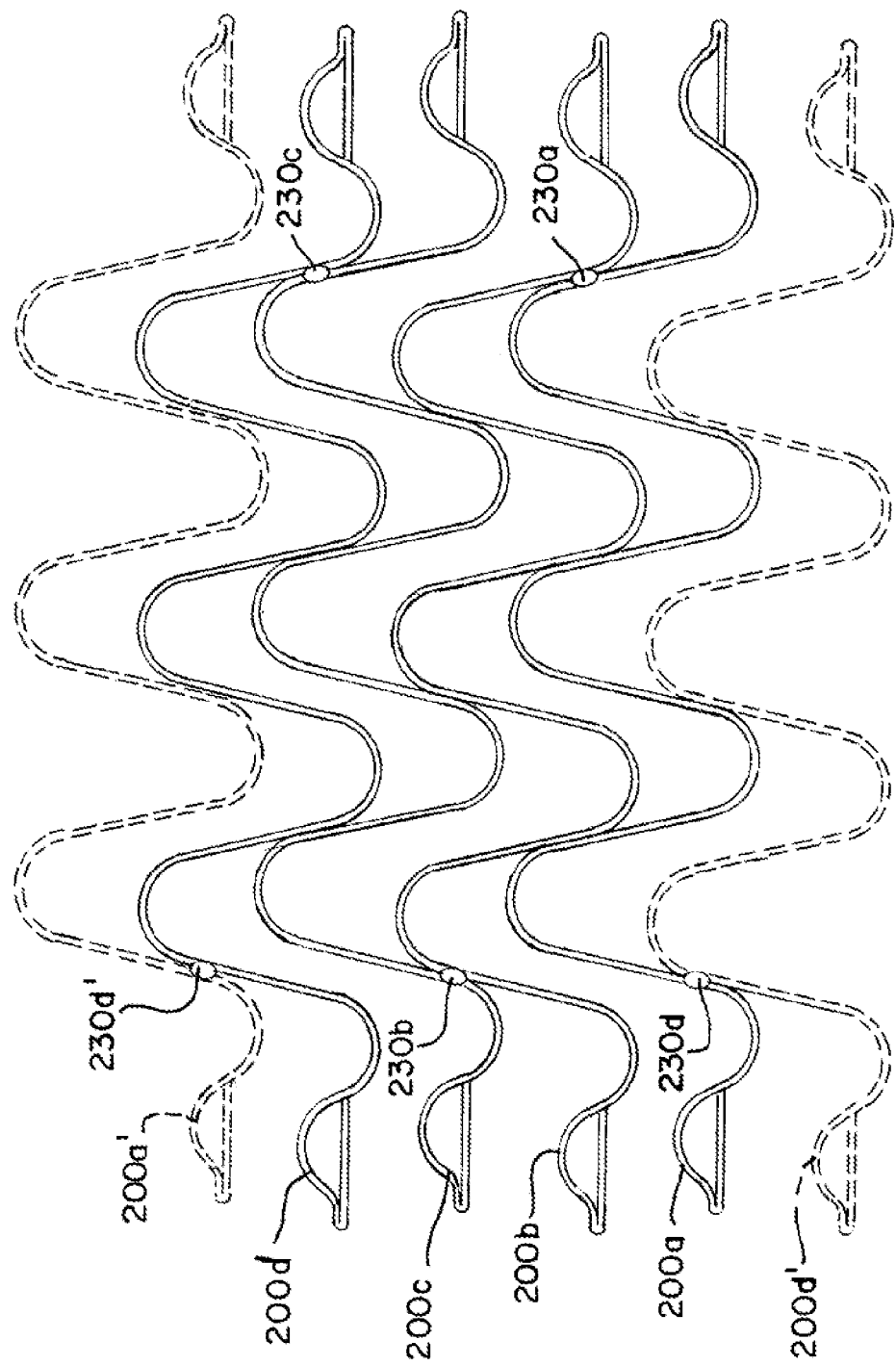
Figure 10A:
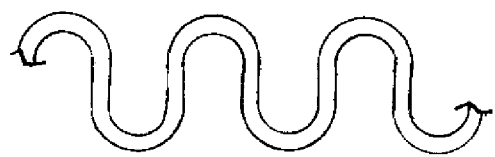
FIGS. 10A to 10E illustrate example waveform patterns or undulating patterns for a wire of a stent according to the present invention.
Figure 10B:
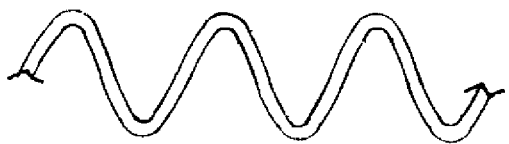
Figure 10C:
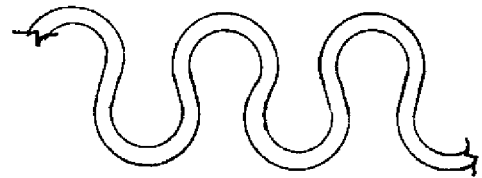
Figure 10D:
Figure 10E:
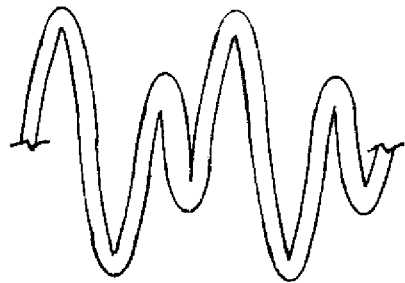

FIG. 6 is a two-dimensional illustration of four wires placed to define a circumference of a stent having one joint 230a, 230b, 230c, 230d, 230d' connecting each pair of adjacent wires. As will be appreciated and understood, the joints 230a, 230b, 230c, 230d, 230d' can be positioned at any number of locations. FIG. 6 illustrates an alternative configuration of the four wires 200a, 200b, 200c, 200d, illustrated in FIG. 5 and the four joints 230a, 230b, 230c, 230d. As will be appreciated and understood, any number of joints can be used to connect any number of wires to achieve a desired flexibility, structural integrity, and conformability for the stent. Minimal connections 230a, 230b, 230c, 230d can allow the wires 200a, 200b, 200c, 200d to move independently of each other over a majority of the length of the stent.

FIG. 7 is a two-dimensional illustration of four wires placed to define a circumference of a stent such that the wires are interwoven to define a circumference of the stent. Each wire can cross over and under each neighboring wire. As illustrated, a first wire 200a can cross under 244 a first neighboring wire 200d' and over 246 the same wire 200d' within one period of oscillation of the first wire 200a. The first wire 200a can cross under 242 a second neighboring wire 200b and over 248 the second neighboring wire 200b within the same period of oscillation of the first wire 200a. The interwoven structure of the wires 200a, 200b, 200c, 200d can be sufficient to maintain the structural integrity of the stent absent any joints to affix wires. The wires can therefore be independently formed and independently movable. As will be appreciated and understood wires 200a, 200b, 200c, 200d can be intertwined with other wave patterns in any number of patterns.

FIG. 8 is a two-dimensional illustration of four wires placed to define a circumference of a stent such that the wires are interwoven to define a circumference of the stent like the one as illustrated in FIG. 7. A stent can have both interwoven wires 200a, 200b, 200c, 200d, and joints 230a, 230b, 230c, 230d to join neighboring wires. As illustrated, a joint 230b can be placed to connect a first wire 200c and a second wire 200b at a cross-over point. The joints 230a, 230b, 230c, 230d can be placed near an end of the wire, and only one joint can be used to connect each wire to each adjacent wire. As will be appreciated and understood, any number of joints can be used to connect wires and various locations along the length of the stent. Minimal connections 230a, 230b, 230c, 230d can allow the wires 200a, 200b, 200c, 200d to move independently of each other over a majority of the length of the stent.

FIG. 9 is a two-dimensional illustration of four wire segments 200a, 200b, 200c, 200d joined by three bends 230, wherein the wire segments are placed to define a circumference of a stent and each wire segment 200a, 200b, 200c, 200d is joined to a neighboring segment by a bend 230. As illustrated, each bend 230 can be positioned at either a first or second open end of the stent to connect a first wire 200a and a second wire 200b. Connected thusly, the wire segments 200a, 200b, 200c, 200d can be joined to form a contiguous wire characterized by longitudinal undulating segments 200a, 200b, 200c, 200d that are joined alternatively at bends 230 positioned at each end of the stent. The contiguous wire can include atraumatic ends 220 positioned at an end of a first wire segment 200a and an end of a last wire segment 200d in the chain of segments. Alternatively (not shown), the stent can be constructed with multiple independent wires consisting of wire segments joined at bends. Wires and wire segments can be otherwise joined or interwoven as described in other examples presented herein or as known in the art.

FIGS. 10A to 10E illustrate example waveform patterns or undulating patterns for a wire of a stent that can be used in addition to or in place of other waveforms depicted and described herein. As will be appreciated and understood, and number of waveform patterns can be utilized to achieve a desired flexibility, structural integrity, and conformability for the stent, including those not shown, and as known in the art.

Figure 11:
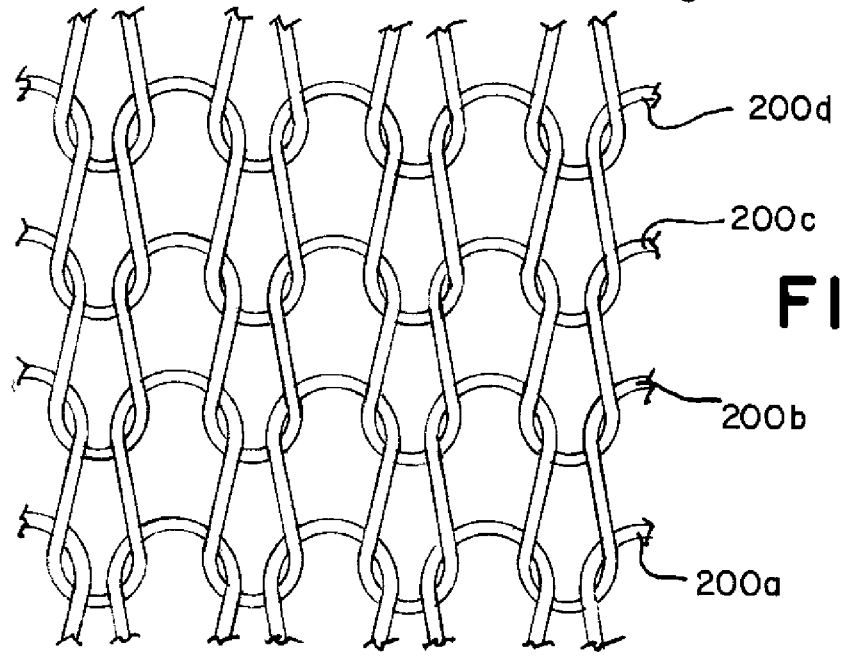
FIG. 11 illustrates an example wire weave pattern of a stent according to the present invention.

FIG. 11 illustrates an example wire weave pattern that could be utilized to form a stent in addition to or in place of other weave patterns depicted and described herein.

Figure 12A:
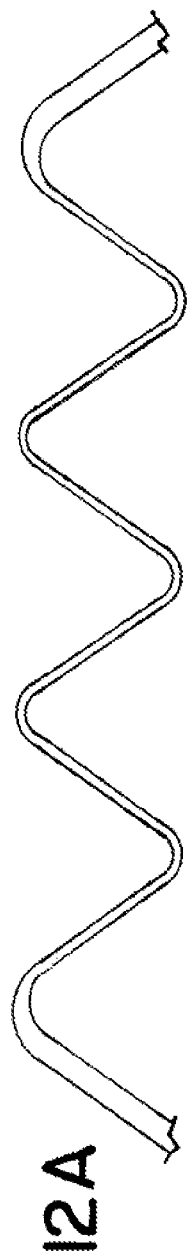
FIGS. 12A to 12D illustrate example wire segments having a variable width according to the present invention.
Figure 12B:
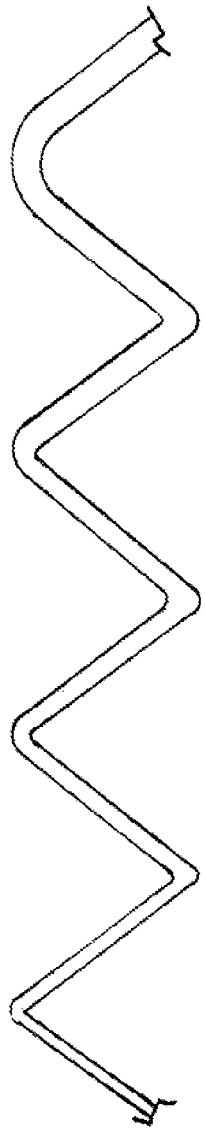
Figure 12C:
Figure 12D:

FIGS. 12A to 12D illustrate example wire segments having a variable width that could be utilized to form a stent in addition to or in place of other wire features depicted and described herein. As illustrated in FIG. 12A, a wire can have an undulating pattern having thicker segments near each end of the wire and thinner segments positioned in the middle of the wire. Thinner central segments can allow the stent to pass more easily through a microcatheter while thicker end segments can improve structural integrity at the stent ends for anchoring within a body lumen. As illustrated in FIG. 12B, a wire can have thin segments near one end and thicker segments at the other end. As illustrated, the segments can become increasingly thicker or thinner from one end of the wire to the other. Stents formed from wire segments with progressively changing segment thickness can be formed to have a tapered structure that can be advantageous for achieving conformity to the walls of a body lumen when implanted in a body lumen that is tapered.

The descriptions contained herein are examples of embodiments of the invention and are not intended in any way to limit the scope of the invention. As described herein, the invention contemplates many variations and modifications of the stent, including alternative shapes for oscillating portions of wires, alternate shapes for atraumatic end segments of wires, alternative means of joining or connecting wires, alternative patterns for interlacing wires to form the stent, forming stents with any number of wires, or utilizing any of numerous materials or manufacturing means for the stent, for example. These modifications would be apparent to those having ordinary skill in the art to which this invention relates and are intended to be within the scope of the claims which follow.

The invention claimed is:

1. A stent comprising:
   a stent length measured from a first open end to a second open end;
   two or more wires each comprising a three-dimensional oscillating portion, the oscillating portion comprising:
      an oscillating portion length measured parallel to a z-axis;
      a curvature extending circumferentially through an arc of less than 360° about the z-axis, extending the length of the oscillating portion, and maintaining a substantially constant radius from the z-axis over the oscillating portion length; and
      a waveform oscillating circumferentially, confined within the arc of the curvature, and extending over the oscillating portion length; and
   a first joint affixing a first wire of the two or more wires to a second wire of the two or more wires approximate the first open end, the first joint being the only affixed joint between the first wire and the second wire,
   wherein the oscillating portion length extends a majority of the stent length;
   wherein the oscillating portion of each of the two or more wires is movable independent of the oscillating portion of every other of the two or more wires;
   wherein the stent is movable from a collapsed configuration that is stretched lengthwise and has a smaller diameter to an expanded configuration that is compressed lengthwise and has a larger diameter; and
   wherein the waveform of each of the two or more wires comprises undulations, the undulations of each wire recessing circumferentially within undulations of at least one of a circumferentially adjacent wire such that the circumferential positioning of the undulating wires defines a circumference of the stent.

2. The stent of claim 1, wherein each of the two or more wires crosses under and crosses over the at least one circumferentially adjacent wire at least once within one period of undulation of the waveform of the first wire.

3. The stent of claim 1, wherein each of the two or more wires is independently formed from every other of the two or more wires.

4. The stent of claim 1, further comprising:
   a first end structure positioned adjacent the first open end, extending between the first open end and the oscillating portion of each of the two or more wires; and
   a second end structure positioned adjacent the second open end, extending between the second open end and the oscillating portion of each of the two or more wires.

5. The stent of claim 4, wherein the first end structures and the second end structures each comprises an atraumatic shape.

6. The stent of claim 1, wherein a wire of the two or more wires has a width that varies along the length of the stent.

7. The stent of claim 1, wherein the stent comprises three or more wires.

8. A stent comprising a tubular structure comprising:
   a plurality of wires each comprising an undulating wire segment and an atraumatic wire segment,
   wherein the plurality of wires are positioned circumferentially to form the tubular structure,
   wherein the undulating wire segments extend over a majority of a length of the stent, the undulating wire segments each comprising undulations oscillating circumferentially, the undulations of each of the undulating wire segments recessing circumferentially within undulations of at least one of the circumferentially adjacent undulating wire segments such that the circumferential positioning of the undulating wire segments defines a circumference of the stent,
   wherein the atraumatic wire segments are each positioned approximate a first end or a second end of the stent, and
   wherein each wire of the plurality of wires is joined to a first circumferentially adjacent wire at only one joint, and
   wherein each wire of the plurality of wires is joined to a second, oppositely circumferentially adjacent wire of the plurality of wires at only one joint.

9. The stent of claim 8, wherein each of the plurality of wires comprises two of the atraumatic wire segments, one atraumatic wire segment at each end of the wire, and one of the undulating wire segments extending between the two atraumatic wire segments.

10. The stent of claim 8, wherein each of the plurality of wires comprises a width that varies along a length of the respective wire.

11. The stent of claim 8, wherein a first wire of the plurality of wires crosses under and crosses over the at least one circumferentially adjacent wire of the plurality of wires at least once within one period of undulation of the waveform of the first wire.

* * * * *